(12) United States Patent
Bevirt et al.

(10) Patent No.: US 6,399,024 B1
(45) Date of Patent: Jun. 4, 2002

(54) MULTICHANNEL PIPETTE HEAD

(75) Inventors: JoeBen Bevirt, Emerald Hills, CA (US); Josh Guyot, Fly Creek, NY (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/495,489

(22) Filed: Feb. 1, 2000

(51) Int. Cl.[7] .................................................. G01N 1/14
(52) U.S. Cl. ................. 422/100; 73/864.01; 73/864.13; 73/864.16; 73/864.17; 73/864.32
(58) Field of Search ........................ 422/100; 73/864.01, 73/864.13, 864.14, 864.16, 864.17, 863.32

(56) References Cited

U.S. PATENT DOCUMENTS

| | | |
|---|---|---|
| 4,106,911 A | 8/1978 | Marcelli |
| 4,478,094 A | 10/1984 | Salomaa et al. |

FOREIGN PATENT DOCUMENTS

| | | |
|---|---|---|
| WO | 99/26723 | 6/1999 |

Primary Examiner—David A. Reifsnyder
(74) Attorney, Agent, or Firm—Richard Aron Osman

(57) ABSTRACT

The invention provides multichannel pipette heads and autopipettors for loading, measuring, transporting and dispensing, particularly from one micro-plate to another. An exemplary multichannel pipette head comprises a pump housing, pistons, a drive plate, an aspiration drive and bearing rails, wherein the pump housing comprises chambers adapted to receive the pistons, the pistons each comprise a shaft, the drive plate retains the pistons and translocates the piston shafts through chambers, the aspiration drive translocates the drive plate along the bearing rails which pass through the drive plate and attach to the pump housing.

21 Claims, 9 Drawing Sheets

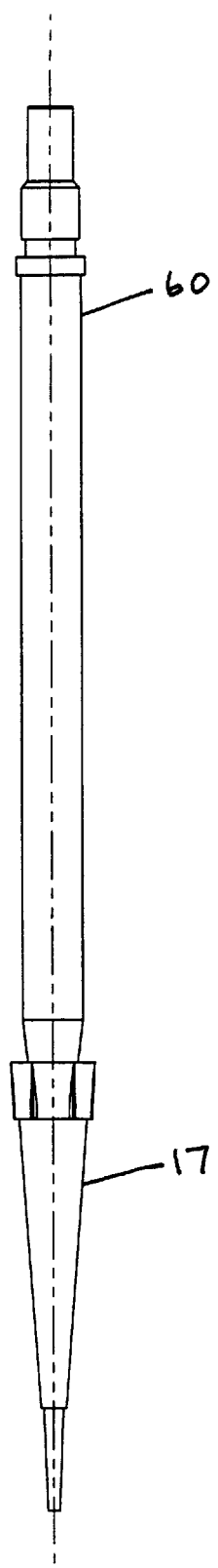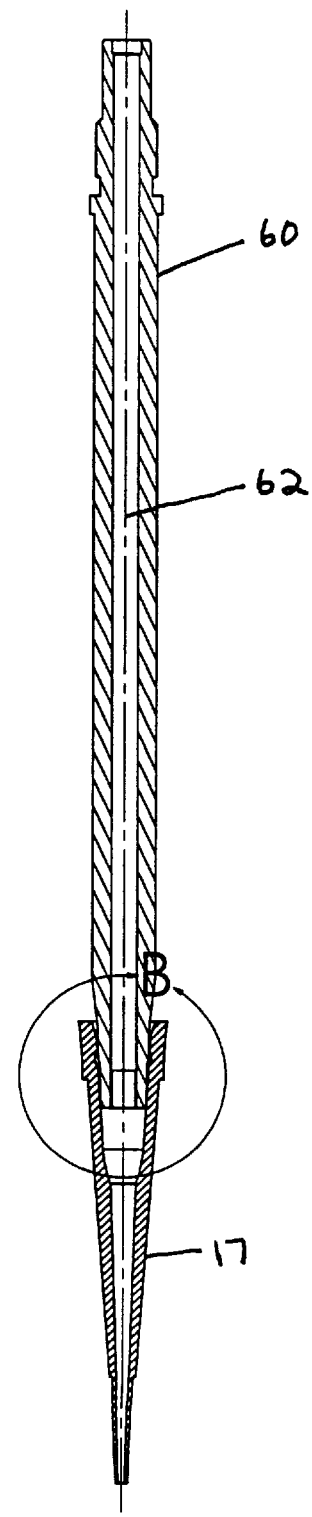
FIGURE 6B  FIGURE 6C

MULTICHANNEL PIPETTE HEAD

INTRODUCTION

1. Field of the Invention

The invention is in the field of multichannel pipette heads for measuring and transporting fluids.

2. Background

Automated multichannel liquid dispensing pipettors provide a broad range of applications in biotechnology, medicine and analytical chemistry. The invention provides an improved head for multichannel pipettors.

SUMMARY OF THE INVENTION

The invention provides methods and devices for measuring and transporting fluids, particularly from one microplate to another. Devices encompassed by the disclosure are more specifically defined in the following claims 1. A multichannel pipette head comprising a pump housing, pistons, a drive plate, an aspiration drive and bearing rails, wherein the pump housing comprises chambers adapted to receive the pistons, the pistons each comprise a shaft, the drive plate retains the pistons and translocates the piston shafts through chambers, the aspiration drive translocates the drive plate along the bearing rails which, preferably pass through the drive plate, and attach to the pump housing.

2. A multichannel pipette head according to claim 1, wherein aspiration drive is an on-board drive comprising a unified ball screw, motor shaft and bearing shaft and rotatably, axially and operably attached thereto, a rotor of a motor, preferably a brushless DC motor, preload bearings and a bearing preload nut for securing the preload bearings.

3. A multichannel pipette head according to claim 1, wherein aspiration drive is an on-board drive comprising a unified ball screw, motor shaft and bearing shaft and axially and operably attached thereto, a position sensor and the pipette head preferably further comprises a digital encoder assembly, wherein the position sensor rotates through the digital encoder assembly.

4. A multichannel pipette head according to claim 1, further comprising within each chamber, a nipple having a proximal end adapted for coupling to the head, a distal end adapted for coupling to a pipette tip and an axial bore terminating at proximal and distal end apertures, wherein the proximal end aperture is exposed on the proximal surface of the head and the distal end aperture is exposed on the distal surface of the head, wherein the drive plate translocates the pistons through the nipples.

5. A multichannel pipette head according to claim 1, further comprising within each chamber, a nipple having a proximal end adapted for coupling to the head, a distal end adapted for coupling to a pipette tip and an axial bore terminating at proximal and distal end apertures, wherein the proximal end aperture is exposed on the proximal surface of the head and the distal end aperture is exposed on the distal surface of the head, wherein the drive plate translocates the pistons through the nipples, wherein the pump housing comprises a discrete nipple retainer plate into which the proximal end of each nipple is retained by threads.

6. A multichannel pipette head according to claim 1, further comprising within each chamber, a nipple having a proximal end adapted for coupling to the head, a distal end adapted for coupling to a pipette tip and an axial bore terminating at proximal and distal end apertures, wherein the proximal end aperture is exposed on the proximal surface of the head and the distal end aperture is exposed on the distal surface of the head, wherein the drive plate translocates the pistons through the nipples, wherein the pistons each further comprise a proximal end ball and the drive shaft retains the end ball of each piston in a recess secured by a set screw.

7. A multichannel pipette head according to claim 1, further comprising within each chamber, a nipple having a proximal end adapted for coupling to the head, a distal end adapted for coupling to a pipette tip and an axial bore terminating at proximal and distal end apertures, wherein the proximal end aperture is exposed on the proximal surface of the head and the distal end aperture is exposed on the distal surface of the head, wherein the drive plate translocates the pistons through the nipples, wherein the axial bore contains a friction-reducing plastic sleeve through which the piston translocates.

8. A multichannel pipette head comprising a pump housing and a stripper plate comprising spring loaded actuating columns topped by retention collars, wherein the stripper plate is suspended from the pump housing from the collars and by the columns whereby the collars protrude above the pump housing.

9. A multichannel pipette head comprising a bar code reader adapted to reading a bar code affixed to a microtiter plate.

10. A multichannel pipette head comprising a latch for releasing a electromechanical coupling comprising a suspension bracket and an electronic connector, which together operatively join the pipette head to an autopipettor.

11. A multichannel pipette head comprising nipples adapted for attaching a pipette tip, each nipple having a proximal end adapted for coupling to the head, a distal end adapted for coupling to the pipette tip and an axial bore terminating at proximal and distal end apertures, wherein the distal end aperture comprises a non-circular configuration adapted to tool receipt to enable rotation of the nipple.

12. A multichannel pipette head comprising nipples adapted for attaching a deformable pipette tip, each nipple having a proximal end adapted for coupling to the head and a distal end adapted for coupling to the pipette tip, wherein the distal end comprises a proximal taper and a distal taper and the pipette tip comprises a thicker walled proximal portion proximate to a receiving opening and a thinner walled distal portion proximate to an axially opposite dispensing opening, wherein the distal end is configured to insert into the receiving opening of the pipette tip whereby the distal taper contacts and deforms the distal portion of the pipette tip and the proximal taper contacts and deforms the proximal portion of the tip wherein the deformation at the distal portion of the pipette tip is greater than the deformation at the proximal portion of the pipette tip and thereby reversibly couples the pipette tip to the distal end of the nipple.

13. A multichannel pipette head according to claim 12, wherein the proximal taper is flatter than the distal taper.

14. A multichannel pipette head according to claim 12, wherein the proximal taper is offset inwardly from the distal taper.

15. A multichannel pipette head according to claim 12 further comprising a deformable pipetted tip reversibly coupled to the distal end of the nipple.

16. A multichannel pipette head comprising any combination of the limitations the foregoing claims, e.g. a multichannel pipette head according to claim 3, further described by the limitations of claims 8, 10 and 12.

17. An autopipettor comprising a multichannel pipette head as described by any of the foregoing claims.

18. An autopipettor comprising a multichannel pipette head as described by any of the foregoing claims, and further comprising a pipette head attachment assembly, and functional tray stations, wherein the autopipettor is adapted to functionally engage the pipette head with the tray stations, such as by positioning pipette tips over a station-secured microtiter plate and optionally, wherein the pipette head is reversibly electro-mechanically coupled to the head attachment assembly.

A method for loading pipette tips or loading and/or dispensing fluid, comprising the step of loading pipette tips on a pipette head described in any of the foregoing claims and/or dispensing fluid with a pipette head or autopipettor as described in any of the foregoing claims.

BRIEF DESCRIPTION OF THE FIGURES

FIGS. 6A–6D provide various views of a nipple: FIG. 6A shows a nipple in three-dimensions; FIG. 6B shows a nipple with an attached pipette tip in two-dimensions; FIG. 6C provides a cross-sectional view of the nipple and pipette tip; and FIG. 6D is an enlarged view of the demarcated region B of FIG. 6C.

DETAILED DESCRIPTION OF PARTICULAR EMBODIMENTS OF THE INVENTION

Figure 1:
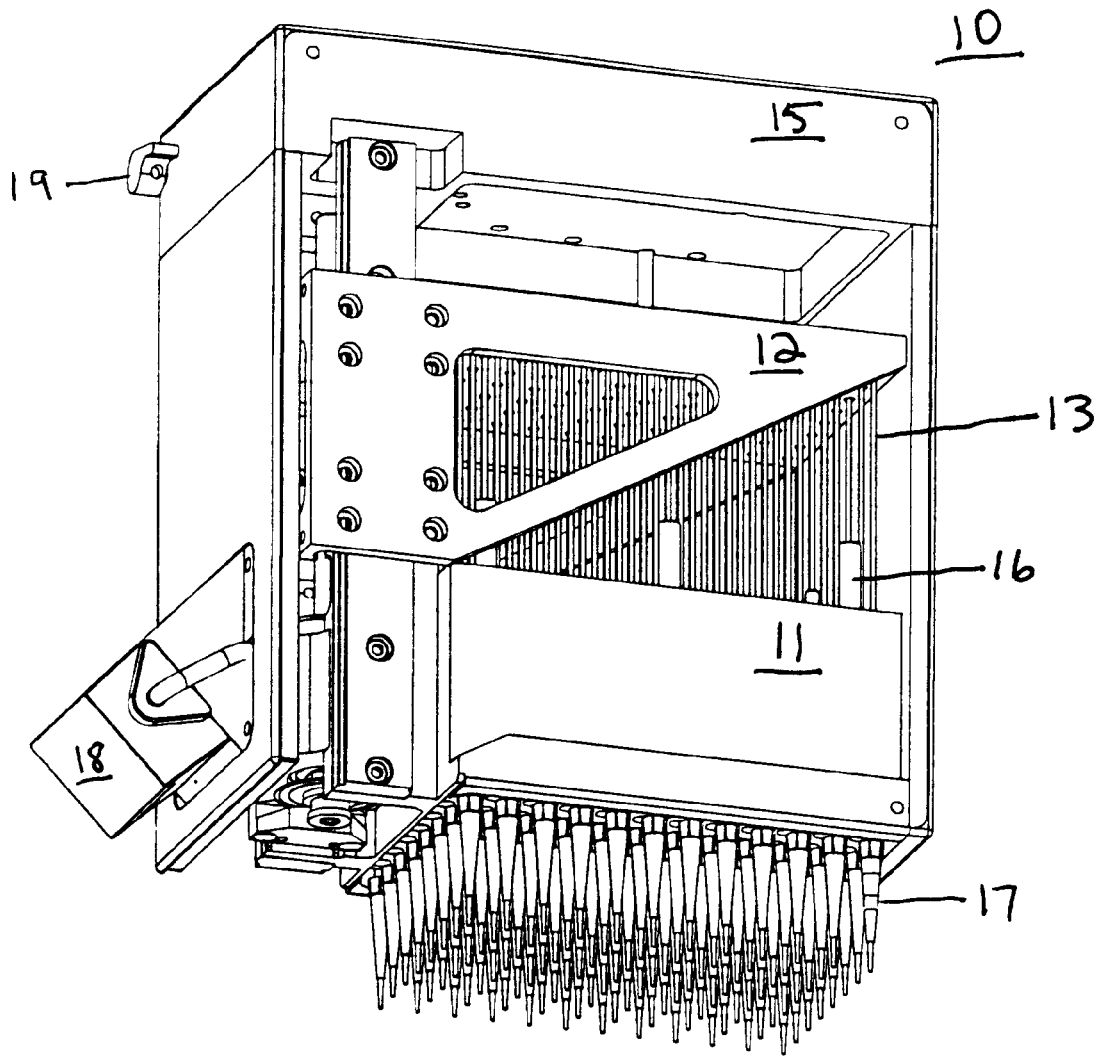
FIG. 1 shows a pipette head.

The following descriptions of particular embodiments and examples are offered by way of illustration and not by way of limitation.

In one aspect, the head provides a full-length nipple. This design feature eliminates concentricity problems associated with boring through long spans (e.g. 2 inches) of pump housing material (e.g. aluminum). The nipples function to hold the pipette tips, define the piston bore, and maintain alignment between the tips.

In another aspect, the head provides ball end pistons for alignment. Each piston has a ball end which rests in a tapered bore of a drive plate and is secured by a set screw. This design feature allows the piston to move in two axes of rotation while being held securely in the third and in all three translational axes of motion. A seal is formed by an O-ring at distal end of cylinder. In a alternative embodiment, spring energized Teflon seals around the piston diameter are used instead of O-rings. Note that all pistons are held and actuated by a single drive plate.

In another aspect, the head provides nipple bore liner sleeves for receiving the piston shafts. The sleeves are of a friction-reducing material such as a plastic (e.g. Teflon) and reduce friction within the nipple bore. This design feature also reduces the dead air volume within the sealed cavity of the nipple thus increasing the accuracy and precision of the pipette head. In an alternative embodiment, the head does not provide separate nipples and a plastic tube lining is inserted directly into bored holes of the pump housing.

In another aspect, the nipples of the head have an extraction tool feature. Within the distal end of each nipple has been cut a keyed slot which allows, with the use of the corresponding keyed tool, the user to remove the nipple from the assembly. The keyed tool may be configured to removed nipples individually or en mass (e.g. 96 at once). Alternatively, the entire nipple assembly can also be removed by taking off the nipple retainer plate. This design feature allows the easy servicing of individual nipples or the servicing of all the nipples at once.

In another aspect, the nipples of the head have a dual taper distal end for engaging a pipette tip. The distal taper is configured to contact the inner wall of the pipette tip where the wall is thinner, below the upper collar of the pipette tip and the proximal taper is configured to contact the inner wall of the pipette tip in the thicker, collar region. The tapers are configured to require less deformation of the tip walls at the collar region as the distal end of the nipple is inserted into the pipette tip for loading the tip onto the nipple. This may be effected, for example, by providing a flatter proximal taper or by offsetting the proximal tapper inwardly (toward the nipple bore) relative to the distal taper. By minimizing the amount of deformation required at the thicker collar region of the pipette tip, this design feature minimizes the amount of pressure required to load the pipette tips.

In another aspect, the head provides an integrated design, i.e. a single block serves as cylinder housing, motor housing, bearing mount, and primary support structure. This design feature provides reduced size, weight, part count, and assembly time in addition to increased speed, accuracy, repeatability, reliability, and stiffness. In a particular embodiment, this design employs linear bearings, which further maximize stiffness.

In another aspect, the head is configured with an on-board aspiration drive that unifies ball-screw, motor-shaft, and bearing shaft. The screw is retained axially by two or more preloaded bearings. This design feature reduces size, weight, part count, and assembly time and increases speed, accuracy, repeatability, reliability, and stiffness. Note that no coupling or belt is necessary, i.e. the screw and motor shaft are one material element. In particular embodiments, a position sensor is attached directly to the screw shaft, rather than to a distinct motor shaft and the head is configured with a brushless DC motor.

In another aspect, the head provides a stepped stripping plate for removing pipette tips from the nipples. In this design, stripping plate thickness is incrementally varied such that pipette tips are stripped two columns at a time, decreasing the total force needed. Actuation may be achieved by retraction of piston drive plate hitting on spring loaded pipette tip stripper plate columns.

Referring to the Figures, FIG. 1 shows a pipette head 10 comprising a pump housing 11 and a drive plate 12 which translocates pistons 13 through chambers (not visible) of the pump housing 11. The drive plate 12 is translocated by an on-board aspiration drive (mostly obscured by proximal bearing rail) along bearing rails 14 that pass through the drive plate 12 and attach to the pump housing 11 and a head coupling assembly 15. Protruding from the top surface of the housing are collars 16 of suspended and spring loaded stripper plate columns (not shown). Protruding from the bottom surface of the housing and covered by pipette tips 17 are distal ends (obscured by pipette tips) of nipples (not visible) retained in the chambers (not visible). Affixed to the head is a bar code reader 18. Also shown is a latch 19 for releasing a mechanical coupling (not visible) which joins the head 10 to an autopipettor (not shown).

Figure 2:
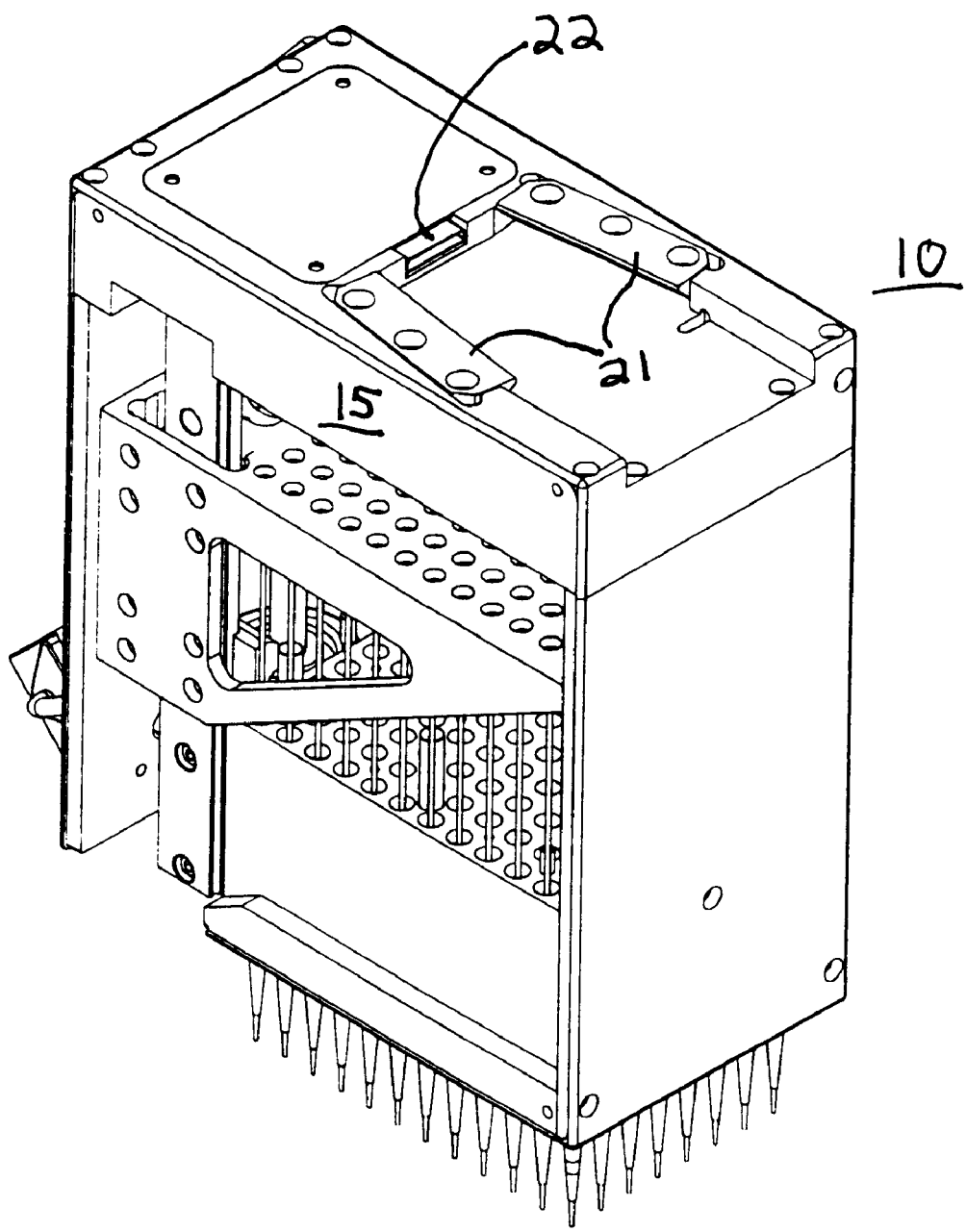
FIG. 2 provides a different view of the pipette head.

FIG. 2 provides a different view of the pipette head 10, showing the coupling assembly 15 which joins the head 10 to an autopipettor (not shown). The coupling assembly 15 comprises to suspension brackets 21 and an electronic connector 22 for mechanically and electronically attaching the head 10 to an autopipettor (not shown).

Figure 3:
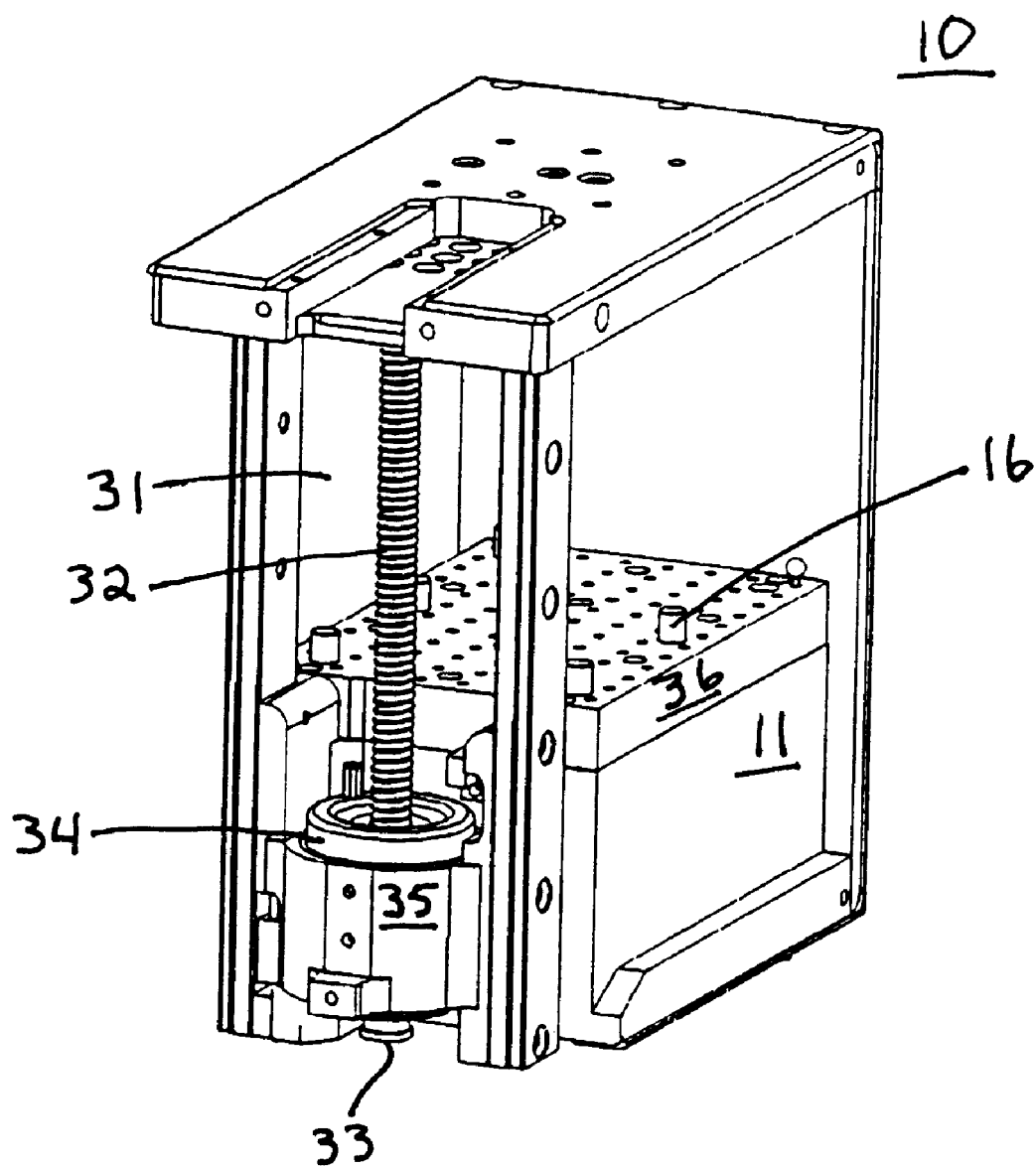
FIG. 3 shows the pipette head without a drive plate.

FIG. 3 shows the pipette head 10 without a drive plate (not shown). This view shows directly coupled to a pump housing 11, an on-board aspiration drive 31 comprising a bearing shaft 32 having a distal terminus 33 and a rotor of a DC brushless motor 34, mostly obscured by a motor bracket 35 joined to an extension of the pump housing 11. In the embodiment shown, the pump housing 11 comprises a discrete nipple retainer plate 36 from which collars 16 of the suspended and spring loaded stripper plate columns (not visible) protrude.

Figure 4:
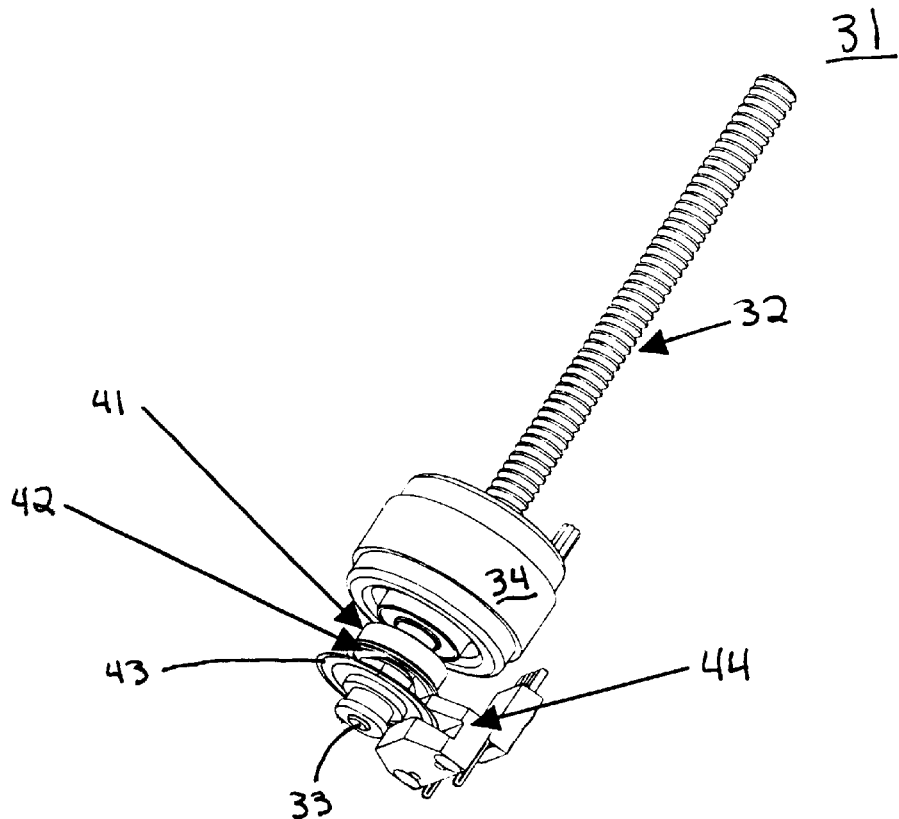
FIG. 4 shows the on-board aspiration drive.

FIG. 4 shows the on-board aspiration drive 31 comprising a unified ball screw, motor shaft and bearing shaft 32 having a distal terminus 33, a stator to brushless DC motor 34, preload bearings 41, a bearing preload nut 42 and a position sensor 43 which rotates through a digital encoder assembly 44.

Figure 5:
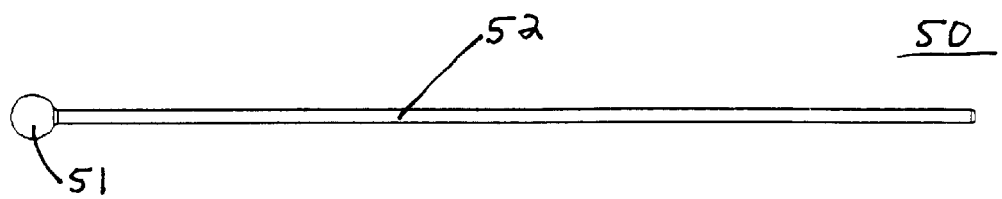
FIG. 5 shows an individual isolated piston.

FIG. 5 shows an individual isolated piston 13 comprising a proximal end ball 51 and a shaft 52.

Figure 6A:
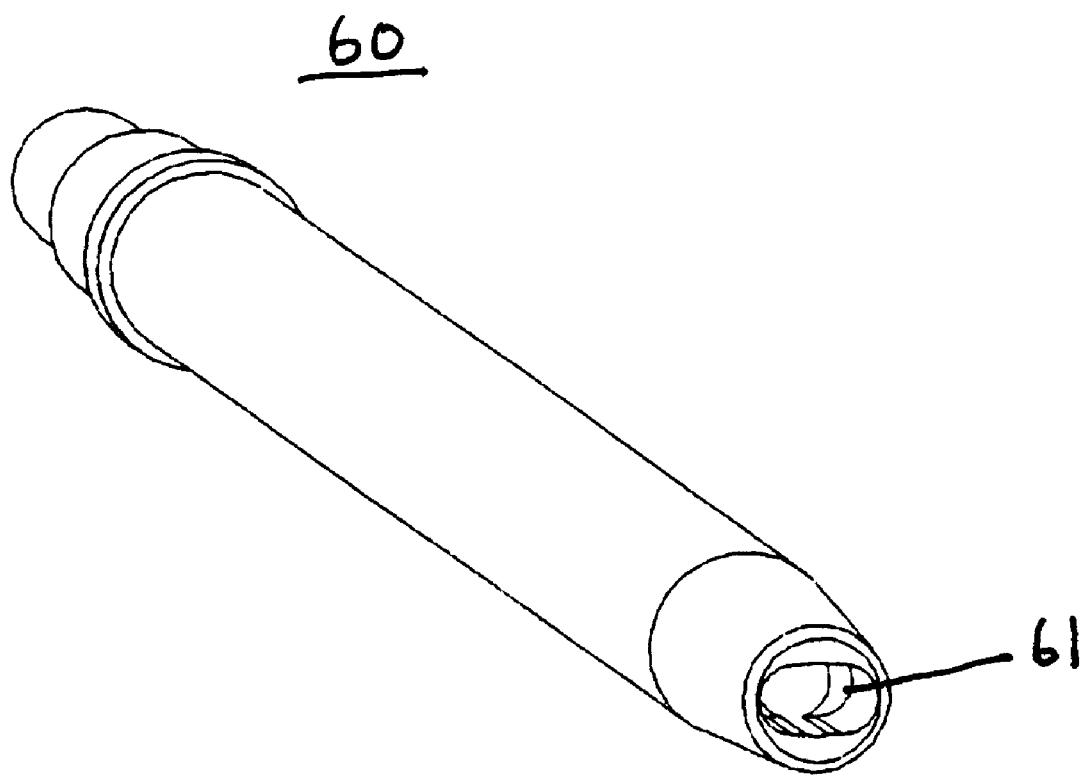
Figure 6D:
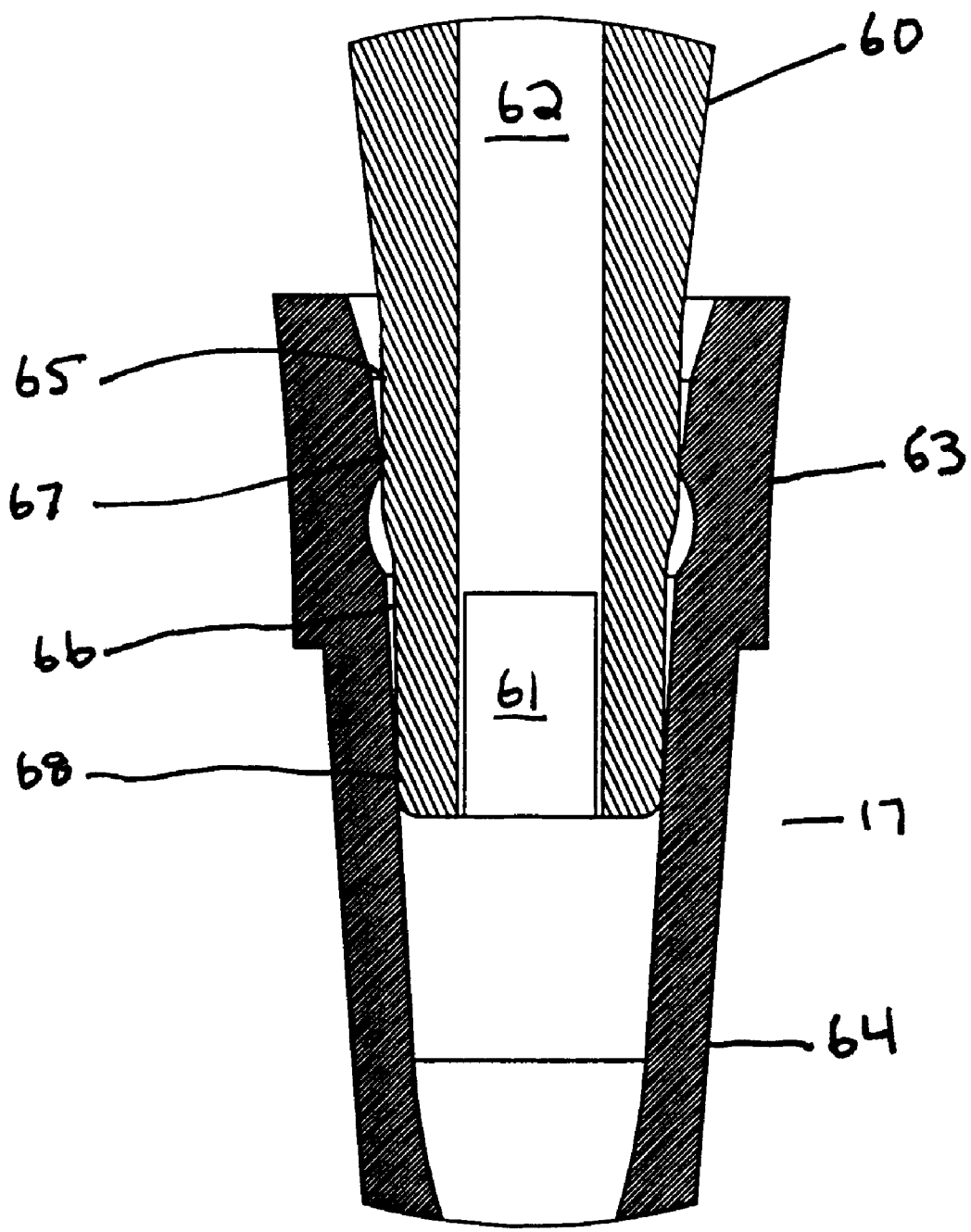

FIGS. 6A–6D provide various views of a nipple 60. FIG. 6A shows a nipple 60 in three-dimensions, including a keyable slot 61 of the distal aperture of the nipple 60. FIG. 6B shows a nipple 60 in two-dimensions, including a pipette tip 17 attached to the distal end of the nipple 60. FIG. 6C provides a cross-sectional view of the pipette tip 17 attached to the distal end of the nipple 60 and additionally shows the bore 62 of the nipple 60. FIG. 6D is an enlarged view of the demarcated region B of FIG. 6C, showing the keyable slot 61 in fluid connection with the bore 62 of the nipple 60 and the thicker collar portion 63 of the pipette tip 17 engaging the proximal taper 65 of the nipple 60 at a proximal contact point 67 and the thinner body portion 64 of the tip 17 engaging the distal taper 66 of a nipple 60 at a distal contact point 68.

Figure 7:
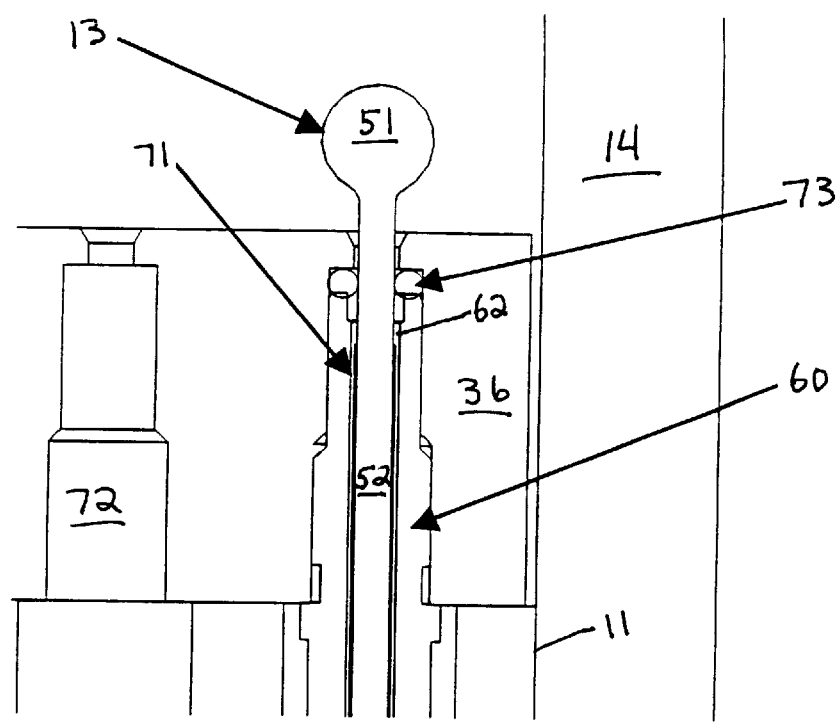
FIG. 7 shows a cross sectional view showing a piston depressed through a plastic sleeve of a bore of a nipple disposed in a chamber of a pump housing.

FIG. 7 shows a cross sectional view showing a piston 13 completely depressed through a plastic sleeve 71 of a bore 62 of a nipple 60 disposed in a chamber 72 of a pump housing 11 disposed along a bearing rail 14. In the embodiment shown, the pump housing 11 comprises a discrete nipple retainer plate 36 into which the proximal end of the nipple 60 is secured by threads (not shown). An O-ring 73 surrounds the piston shaft 52 providing a gas and liquid seal. The piston ball 51 is retained in a recess (not shown) of the drive plate (not shown) and secured therein by a set screw (not shown).

Figure 8:
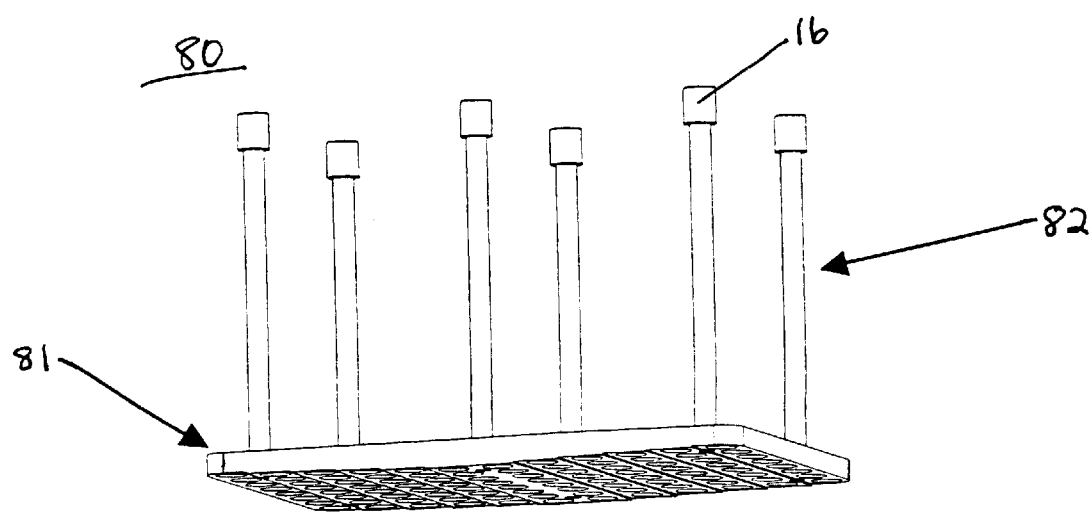
FIG. 8 shows a stripper plate assembly.

FIG. 8 shows a stripper plate assembly 80 comprising a stripper plate 81 and stripper plate actuating columns 82 topped by collars 16.

Figure 9:
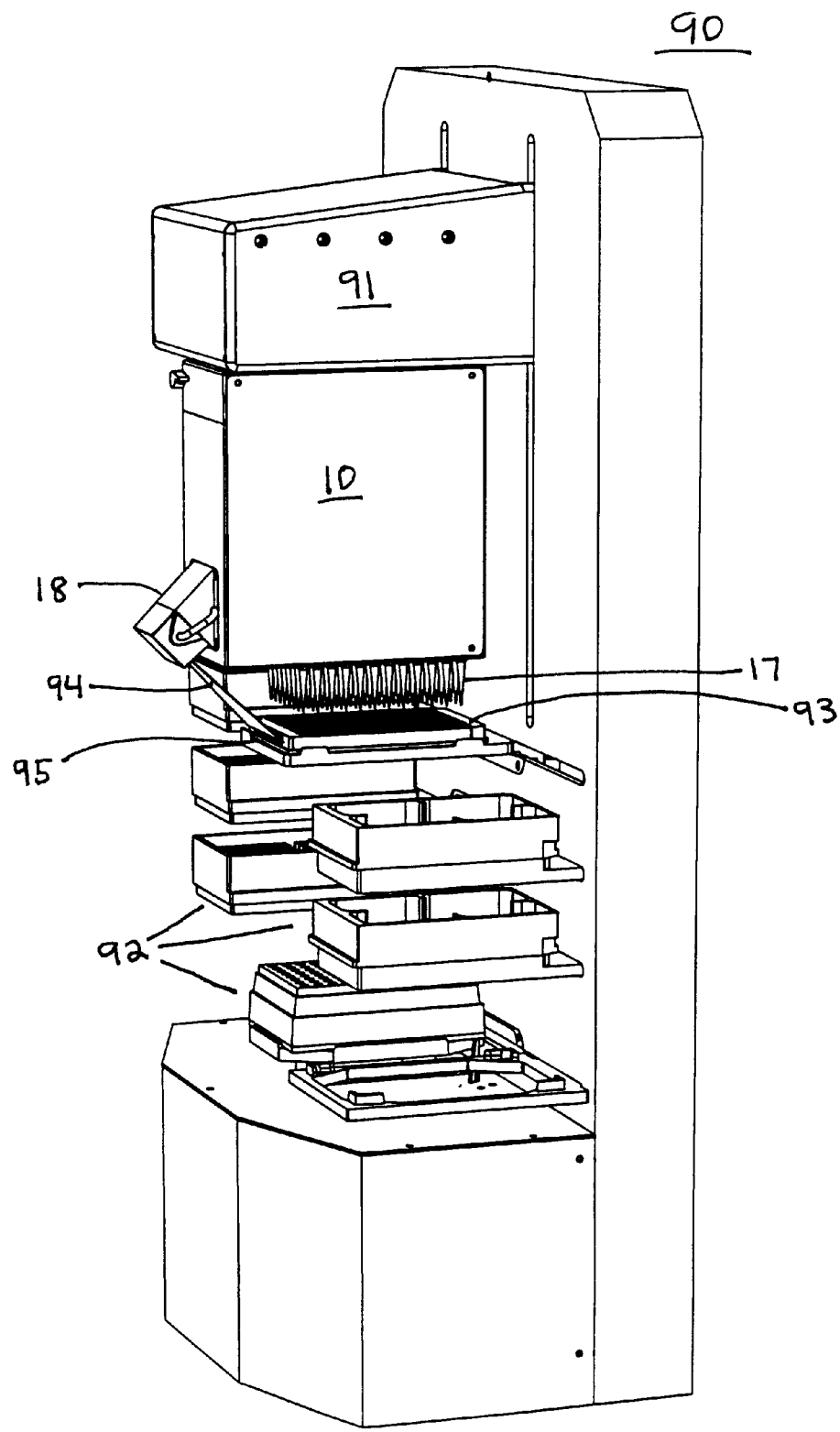
FIG. 9 shows an autopipettor comprising a pipette head as described herein.

FIG. 9 shows an autopipettor 90 comprising a pipette head attachment assembly 91, a pipette head 10, and functional tray stations 92. The autopipettor 90 is adapted to function-ally engage the pipette head 10 with the tray stations 92, such as by positioning pipette tips 17 over a station-secured microtiter plate 93. The pipette head 10 comprises a barcode reader 18 for reading, along a sight-path 94, a barcode 95 affixed to the microtiter plate 93. The pipette head 10 is reversibly electro-mechanically coupled to the head attachment assembly 91.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A multichannel pipette head detachable from, and adapted for coupling to, a pipette head attachment assembly of an autopipettor, said pipette head comprising a pump housing, pistons, a drive plate, an on-board aspiration drive and beating rails, wherein the pump housing is attached to the bearing rails and comprises chambers adapted to receive the pistons, the pistons each comprise a shaft, the drive plate retains the pistons and translocates the piston shafts through chambers, the aspiration drive comprises a unified ball screw, motor shaft and bearing shaft and translocates the drive plate along the bearing rails relative to the pump housing.

2. A multichannel pipette head according to claim 1, wherein the aspiration drive comprises rotatably, axially and operably attached to the unified ball screw, motor shaft and bearing shaft, a rotor of a brushless DC motor, preload bearings and a bearing preload nut for securing the preload bearings.

3. A multichannel pipette head according to claim 1, wherein the aspiration drive comprises axially and operably attached to the unified ball screw, motor shaft and bearing shaft, a position sensor, and the pipette head further comprises a digital encoder assembly, wherein the position sensor rotates through the digital encoder assembly.

4. A multichannel pipette head according to claim 1, further comprising within each chamber, a nipple having a proximal end adapted for coupling to the pump housing, a distal end adapted for coupling to a pipette tip and an axial bore terminating at proximal and distal end apertures, wherein the proximal end aperture is exposed on the proximal surface of the pump housing and the distal end aperture is exposed on the distal surface of the pump housing, wherein the drive plate translocates the pistons through the nipples.

5. A multichannel pipette head according to claim 1, flintier comprising within each chamber, a nipple having a proximal end adapted for coupling to the pump housing, a distal end adapted for coupling to a pipette tip and an axial bore terminating at proximal and distal end apertures, wherein the proximal end aperture is exposed on the proximal surface of the pump housing and the distal end aperture is exposed on the distal surface of the pump housing, wherein the drive plate translocates the pistons through the nipples, wherein the proximal end of each nipple is retained by threads.

6. A multichannel pipette head according to claim 1, further comprising within each chamber, a nipple having a proximal end adapted for coupling to the pump housing, a distal end adapted for coupling to a pipette tip and an axial bore terminating at proximal and distal end apertures, wherein the proximal end aperture is exposed on the proximal surface of the pump housing and the distal end aperture is exposed on the distal surface of the pump housing, wherein the drive plate translocates the pistons through the nipples, wherein the proximal end of each nipple is retained by threads and wherein the pump housing comprises a discrete nipple retainer plate into which the proximal end of each nipple is retained by the threads.

7. A multichannel pipette bead according to claim 1, further comprising within each chamber, a nipple having a proximal end adapted for coupling to the pump housing, a distal end adapted for coupling to a pipette tip and an axial bore terminating at proximal and distal end apertures, wherein the proximal end aperture is exposed on the proximal surface of the pump housing and the distal end aperture is exposed on the distal surface of the pump housing, wherein the drive plate translocates the pistons through the nipples, wherein the proximal end of each nipple is retained by threads, wherein the distal end comprises a non-circular configuration adapted to toot receipt to enable rotation of the nipple.

8. A multichannel pipette head according to claim 1, further comprising within each chamber, a nipple having a proximal end adapted for coupling to the pump housing, a distal end adapted for coupling to a pipette tip and an axial bore terminating at proximal and distal end apertures, wherein the proximal end aperture is exposed on the proximal surface of the pump housing and the distal end aperture is exposed on the distal surface of the pump housing, wherein the drive plate translocates the pistons through the nipples, wherein the axial bore contains a friction-reducing plastic sleeve through which the piston translocates.

9. A multichannel pipette head according to claim 1, wherein the pistons each further comprise a proximal end ball and the drive plate retains the end ball of each piston.

10. A multichannel pipette head according to claim 1, further comprising a stripper plate comprising spring loaded actuating columns topped by retention collars, wherein the stripper plate is suspended from the pump housing from the collars and by the columns whereby the collars protrude above the pump housing.

11. A multichannel pipette head according to claim 1, further comprising a bar code reader adapted to read a bar code affixed to a microtiter plate into or from which the head pipettes.

12. A multichannel pipette bead according to claim 1, further comprising a latch for releasing an integrated electromechanical coupling comprising a suspension bracket and an electronic connector, which together operatively join the pipette head to an autopipettor.

13. A multichannel pipette head according to claim 1, wherein the aspiration drive comprises rotatably, axially and operably attached to the unified ball screw, motor shaft and bearing shaft, a rotor of a brushless DC motor, preload bearings and a bearing preload nut for securing the preload bearings and a position sensor, the pipette head further comprising a digital encoder assembly, wherein the position sensor rotates through the digital encoder assembly; and further comprising within each chamber, a nipple having a proximal end adapted for coupling to the pump housing, a distal end adapted for coupling to a pipette tip and an axial bore terminating at proximal and distal end apertures, wherein the proximal end aperture is exposed on the proximal surface of the pump housing and the distal end aperture is exposed on the distal surface of the pump housing, wherein the drive plate translocates the pistons through the nipples, wherein the proximal end of each nipple is retained by threads, wherein the distal end comprises a non-circular configuration adapted to tool receipt to enable rotation of the nipple, wherein the pistons each further comprise a proximal end ball and the drive shaft retains the end ball of each piston, wherein the head further comprises a stripper plate comprising spring loaded actuating columns topped by retention collars, wherein the stripper plate is suspended from the pump housing from the collars and by the columns whereby the collars protrude above the pump housing, wherein the head further comprises a bar code reader adapted to read a bar code affixed to a microtiter plate into or from which the head pipettes, and wherein the head further comprises a latch for releasing an integrated electromechanical coupling comprising a suspension bracket and an electronic connector, which together operatively join the pipette head to an autopipettor.

14. An autopipettor comprising a multichannel pipette head according to claim 1, a pipette head attachment assembly, and functional tray stations, wherein the autopipettor is adapted to functionally engage the pipette head with the tray stations and the pipette head is reversibly electromechanically coupled to the head attachment assembly.

15. A method for dispensing fluid, comprising the step dispensing fluid with a pipette head according to claim 1.

16. A multichannel pipette head comprising nipples adapted for attaching corresponding pipette tips, each nipple having a proximal end adapted for coupling to the head by threads, a distal end adapted for coupling to the pipette tip and an axial bore terminating at proximal and distal end apertures, wherein the distal end comprises a non-circular configuration adapted to tool receipt to enable rotation and removal of the nipple from the head.

17. A multichannel pipette head according to claim 1, further comprising within each chamber, a nipple having a proximal end adapted for coupling to the pump housing, a distal end adapted for coupling to a deformable pipette tip and an axial bore terminating at proximal and distal end apertures, wherein the proximal end aperture is exposed on the proximal surface of the head and the distal end aperture is exposed on the distal surface of the head, wherein the drive plate translocates the pistons through the nipples, and wherein the distal end comprises a proximal taper and a distal taper and the pipette tip comprises a thicker walled proximal portion proximate to a receiving opening and a thinner walled distal portion proximate to an axially opposite dispensing opening, wherein the distal end is configured to insert into the receiving opening of the pipette tip whereby the distal taper contacts and deforms the distal portion of the pipette tip and the proximal taper contacts arid deforms the proximal portion of the pipette tip wherein the deformation at the distal portion of the pipette tip is greater than the deformation at the proximal portion of the pipette tip and thereby reversibly couples the pipette tip to the distal end of the nipple.

18. A multichannel pipette head comprising nipples adapted for attaching corresponding deformable pipette tips, each nipple having a proximal end adapted for coupling to the pipette head and a distal end adapted for coupling to the pipette tip, wherein the distal end comprises a proximal taper and a distal taper and the pipette tip comprises a thicker walled proximal portion proximate to a receiving opening and a thinner walled distal portion proximate to an axially opposite dispensing opening, wherein the distal end is configured to insert into the receiving opening of the pipette tip whereby the distal taper contacts and deforms the distal portion of the pipette tip and the proximal taper contacts and deforms the proximal portion of the pipette tip wherein the deformation at the distal portion of the pipette tip is greater than the deformation at the proximal portion of the pipette tip and thereby reversibly couples the pipette tip to the distal end of the nipple.

19. A multichannel pipette head according to claim 18, wherein the proximal taper is flatter than the distal taper.

20. A multichannel pipette head according to claim 18, wherein the proximal taper is offset inwardly from the distal taper.

21. A multichannel pipette head according to claim 18 further comprising the deformable pipette tips reversibly coupled to the distal end of the nipple.

* * * * *

UNITED STATES PATENT AND TRADEMARK OFFICE
CERTIFICATE OF CORRECTION

PATENT NO. : 6,399,024 B1
DATED : June 4, 2002
INVENTOR(S) : Bevirt et al.

It is certified that error appears in the above-identified patent and that said Letters Patent is hereby corrected as shown below:

Column 6,
Line 24, "beating" should read -- bearing --;
Line 55, "flintier" should read -- further --;

Column 7,
Line 11, "bead" should read -- head --;
Line 22, "toot" should read -- tool --;

Column 8,
Line 55, "arid" should read -- and --.

Signed and Sealed this

Twenty-eighth Day of January, 2003

JAMES E. ROGAN
*Director of the United States Patent and Trademark Office*